United States Patent
Sun et al.

(10) Patent No.: US 10,836,700 B1
(45) Date of Patent: Nov. 17, 2020

(54) PROCESS FOR PREPARING KETONE OR CARBOXYLIC ACID BY CATALYTIC OXIDATION OF SECONDARY OR PRIMARY ALCOHOL

(71) Applicant: Shanghai Institute of Technology, Shanghai (CN)

(72) Inventors: Xiaoling Sun, Shanghai (CN); Fei Li, Shanghai (CN); Lingjun Ye, Shanghai (CN); Zhilin Tang, Shanghai (CN); Jinxin Zhao, Shanghai (CN); Hehua Li, Shanghai (CN)

(73) Assignee: Shanghai Institute of Technology, Shanghai (CN)

( * ) Notice: Subject to any disclaimer, the term of this patent is extended or adjusted under 35 U.S.C. 154(b) by 0 days.

(21) Appl. No.: 16/850,500

(22) Filed: Apr. 16, 2020

(30) Foreign Application Priority Data

Aug. 26, 2019 (CN) .......................... 2019 1 0790520

(51) Int. Cl.

| | |
|---|---|
| *C07C 51/255* | (2006.01) |
| *C07C 51/235* | (2006.01) |
| *C07C 45/29* | (2006.01) |
| *B01J 31/02* | (2006.01) |
| *B01J 31/18* | (2006.01) |

(52) U.S. Cl.
CPC ......... *C07C 51/255* (2013.01); *B01J 31/0247* (2013.01); *B01J 31/183* (2013.01); *C07C 45/29* (2013.01); *C07C 51/235* (2013.01); *B01J 2231/70* (2013.01); *B01J 2531/845* (2013.01)

(58) Field of Classification Search
CPC ...... C07C 51/255; C07C 51/235; C07C 45/29
See application file for complete search history.

(56) References Cited

U.S. PATENT DOCUMENTS 5,958,821 A * 9/1999 Ishii ...................... B01J 31/006
502/167

OTHER PUBLICATIONS

Murahashi, S. et al. "Aerobic Oxidation of Alcohols with Ruthenium-Cobalt Bimetallic Catalyst in the Presence of Aldehydes." J. Org. Chem., 1993, 58, 7318-7319. American Chemical Society, Washington D.C.

Wang, Y. et al. "Selective catalysis for the oxidation of alcohols to aldehydes in the presence of cucurbit[8]uril." Catalysis Communications, 2011, 12 (12), 1127-1130. Elsevier B,V., The Netherlands.

Baruah, D. et al. "Bi (NO3)3—5H20 and cellulose mediated Cu-NPs—A highly efficient and novel catalytic system for aerobic oxidation of alcohols to carbonyls and synthesis of DFF from HMF." Catalysis Communications, 2016, 77, 9-12. Elsevier B.V., The Netherlands.

Ishii, Y. et al. "A Novel Catalysis of jV-Hydroxyphthalimide in the Oxidation of Organic Substrates by Molecular Oxygen." J. Org. Chem. 1995, 60, 3934-3935. American Chemical Society, Washington D.C.

Chen, B. et al. "Aerobic oxidation of benzyl alcohols using a novel combination of N-hydroxyphthalimide (NHPI) with HNO3 and CuBr2." Res Chem Intermed 2015, 41, 3929-3936. Springer Science+ Business Media Dordrecht.

Hu, Y. et al. "NHPI/tert-butyl nitrite: A highly efficient metal-free catalytic system for aerobic oxidation of alcohols to carbonyl compounds using molecular oxygen as the terminal oxidant." Catalysis Communications, 2016, 83, 82-87. Elsevier B.V., The Netherlands.

Zhou, W. "Aerobic Oxidation of Alcohols to Carbonyl Compounds Catalyzed by N-Hydroxyphthalimide (NHPI) Combined with CoTPP-Zn2Al-LDH." J. Chem. Sci., 2017, 129 (3), 295-299. Indian Academy of Sciences, India.

Rezaeifard, A. et al. "A novel strategy for clean and selective oxygenation of hydrocarbons with n-Bu4NHSO5 in neat water catalyzed by recyclable water-insoluble iron (III) tetraphenylporphyrins." Catalysis Communications, 2011, 12 (8), 761-765, Elsevier B.V., The Netherlands.

* cited by examiner

*Primary Examiner* — Jafar F Parsa
*Assistant Examiner* — Blaine G Doletski
(74) *Attorney, Agent, or Firm* — Olive Law Group, PLLC

(57) ABSTRACT

A process for preparing a ketone or carboxylic acid by catalytic oxidation of a secondary or primary alcohol comprises adding the secondary or primary alcohol as a raw material and N-hydroxyphthalimide (NHPI) combined with phthalocyanine, serving as a catalytic system, into an amount of an organic solvent into which oxygen gas is then introduced, to proceed with an oxidation reaction to give the ketone or carboxylic acid. The oxygen gas is employed as the source of an oxidant. The oxidation reaction may be carried out under normal pressure at 60 to 120° C. for 9 to 36 hours. The process can produce a high yield of ketone or carboxylic acid. Compared with conventional technology, the process has several advantages, such as the green oxidant, the cheap catalyst which can also be easily prepared and separated, and mild reaction conditions, and it is also an environmentally friendly process for alcohol oxidation.

9 Claims, No Drawings

PROCESS FOR PREPARING KETONE OR CARBOXYLIC ACID BY CATALYTIC OXIDATION OF SECONDARY OR PRIMARY ALCOHOL

CROSS REFERENCE TO RELATED APPLICATION

This application claims priority to Chinese Patent Application No. 201910790520.X, filed Aug. 26, 2019, the content of which is incorporated herein by reference in its entirety.

TECHNICAL FIELD

The presently disclosed subject matter relates to the field of green chemical synthesis, in particular to a process for preparing a ketone or carboxylic acid by catalytic oxidation of a secondary or primary alcohol.

BACKGROUND

Conversion of secondary or primary alcohols into ketones or carboxylic acids is one of the most basic and important reactions in organic synthetic chemistry. Selective oxidation of alcohols has been widely used in various fields, such as fine chemical, pharmaceutical synthesis, and flavours and fragrances. Conventional alcohol oxidation reactions typically use transition metal compounds of high valency or hypervalent iodine compounds as an oxidant, which may bring serious pollution to environment. As an environmentally friendly oxidant, molecular oxygen has gained more and more attention. However, activation of molecular oxygen may easily lead to over-oxidation of an oxidation product to generate by-products, such as carbon monoxide and water. Moreover, C—H bonds, which have a high bond energy, are hard to be oxidized with molecular oxygen.

Selective oxidation of secondary or primary alcohols to corresponding ketones or carboxylic acids is one of the most important reactions in organic synthetic chemistry and fine chemical industry. Many processes have been developed using various oxidants such as potassium permanganate ($KMnO_4$), hydrogen peroxide ($H_2O_2$), tert-butyl hydroperoxide (TBHP), and m-chloroperbenzoic acid (m-CPBA) to selectively oxidize secondary or primary alcohols to corresponding ketones or carboxylic acids.

Oxidation of alcohols with molecular oxygen at room temperature in the presence of an aldehyde and $RuCls$-$Co(OAc)_2$ bimetallic catalyst has been reported by Murahashi et al (Murahashi S, et al. Organic Chemistry, 1993, 58(26): 7318-7319.). The aldehyde, as a reducing agent, is contained in the catalytic system, and is finally converted into a carboxylic acid, which leads to additional process steps. Key Laboratory of Macrocyclic and Supramolecular Chemistry of Guizhou Province, Guizhou University has reported oxidation of aryl, allyl, and alkyl alcohols to corresponding aldehydes by o-iodoxybenzoic acid (IBX) in an aqueous solvent (Wang Y H, et al. Catalysis Communications, 2011, 12(12): 0-1130.). This process requires a stoichiometric oxidant and allows only part of the alcohol to be selectively oxidized. Aerobic oxidation of alcohols to carbonyls by using $Bi(NO_3)_3$.$5H_2O$ and cellulose mediated Cu-NPs as a catalytic system has been reported by Diganta et al (Diganta B, et al. Catalysis Communications, 2016, 77: 9-12.). Such a catalytic system contains a transition metal, Bi, which may result in residue of the toxic heavy metal in products.

A process using molecular oxygen as an oxidant and without the need for additives in a stoichiometric amount is very attractive from the viewpoints of sustainable development and environment. Since N-hydroxyphthalimide (NHPI) was first found by Ishii et al to be effective in catalyzing aerobic oxidation of various organic substrates to oxygen-containing compounds, NHPI, which is cheap and of low toxicity, has become a hotspot of research in the field of catalytic oxidation reactions with molecular oxygen serving as an oxidant.

Many catalytic systems associated with NHPI for alcohol oxidation reactions have been proposed in recent years, and have achieved satisfactory results. A NHPI/Co (II or III) catalytic system proposed by Ishii et al (Ishii Y, et al. Tetrahedron Letters. 1995, 35: 6924-6929.) introduces a cobalt salt into the reaction system, which is difficult to recover therefrom and thus leads to a complicated catalyst recovery process due to homogeneity of the catalytic system. A new catalytic system for oxidation of alcohols with oxygen catalyzed by NHPI combined with nitric acid ($HNO_3$) and copper bromide ($CuBr_2$) has been proposed by Chen B. et al (Chen B, et al. Research on Chemical Intermediates, 2015.). This system can effectively catalyze the oxidation of primary benzylic alcohols to corresponding aldehydes with high selectivities. According to this system, $HNO_3$ is required to activate NHPI, causing environment pollution, and the introduction of the transition metal complicates follow-up procedures. A highly practical metal-free catalytic system has been proposed by Yongke Hu et al for aerobic oxidation of alcohols to corresponding ketones and aldehydes using NHPI and tert-butyl nitrite (TBN) with molecular oxygen serving as a terminal oxidant (Yongke Hu, et al. Catalysis Communications. 2016, 83: 82-87.). TBN is extremely unstable, and is easy to decompose in the presence of light. A catalytic system for the aerobic oxidation of alcohols by NHPI combined with cobalt porphyrin intercalated heterogeneous hybrid catalyst (CoTPP-$Zn_2$Al-LDH) has been proposed by Weiyou Zhou et al. Many complicated steps are required to prepare this catalytic system, and the system cannot be practically used very well. Therefore, it is desired to provide an environmentally friendly and cheap catalytic system for catalyzing the oxidation of alcohols at high efficiency and at mild reaction conditions to carbonyl compounds with high yields and selectivities.

SUMMARY

In view of the above problems, an objective of the presently disclosed subject matter is to provide a process for preparing a ketone or carboxylic acid by catalytic oxidation of a secondary or primary alcohol, which at least partially solves the problems in the conventional technology, such as severe environmental pollution caused by conventional oxidants for alcohols, difficult recovery of catalysts, and formation of many by-products, and is an environmentally friendly process for catalytic oxidation of an alcohol.

The above objective of the presently disclosed subject matter is realized by a process for preparing a ketone or carboxylic acid by catalytic oxidation of a secondary or primary alcohol, comprising adding the alcohol and N-hydroxyphthalimide (NHPI) combined with phthalocyanine, serving as a catalytic system, into an organic solvent into which oxygen gas is then introduced, to proceed with an oxidation reaction to give a carbonyl compound.

According to the process of the presently disclosed subject matter, the secondary or primary alcohol is oxidized to the ketone or carboxylic acid with molecular oxygen by a catalytic action of NHPI combined with phthalocyanine. During the reaction, NHPI is converted into phthalimide N-oxyl (PINO) free radicals by heat, which then take hydrogen atoms from hydroxyl groups of the alcohol. The alcohol substrate is then bonded to oxygen atoms activated by phthalocyanine to form the carbonyl compound.

Thanks to both NHPI and phthalocyanine, the oxidation of the secondary or primary alcohol can be well performed with almost no by-product formation. This enables subsequent separations to be easy. Further, the oxidation reaction can be carried out under normal pressure and the carbonyl compound can be produced in a high yield. Oxygen gas, which is widely available and environmentally friendly, allows a reduced cost and an environmentally friendly reaction.

For the catalytic system, NHPI combined with phthalocyanine, at the end of the reaction, phthalocyanine can be separated off by centrifuging and NHPI can be well precipitated after concentration under reduced pressure at a reduced temperature due to its poor solubility. So, the catalyst of the presently disclosed subject matter can be easily recovered.

The catalytic system of the presently disclosed subject matter, NHPI combined with phthalocyanine, comprises NHPI and phthalocyanine. A molar ratio of NHPI to the secondary or primary alcohol may be from about 0.1:1 to about 0.3:1, and a molar ratio of phthalocyanine to the secondary or primary alcohol may be from about 0.04:1 to about 0.1:1.

In examples, the molar ratio of NHPI to the secondary or primary alcohol may be from about 0.2:1 to about 0.3:1, and the molar ratio of phthalocyanine to the secondary to primary alcohol may be from about 0.08:1 to about 0.1:1.

The ratio between the alcohol, NHPI, and phthalocyanine is very important. In view of the effect, if the used amount of NHPI is too small, amounts of the free radials and thus of the activated substrate may be too small, impairing the result of the oxidation reaction; if the used amount of phthalocyanine is too small, the amount of the activated oxygen may be too small, significantly reducing the yield of the target product. On the other hand, if too much NHPI and/or phthalocyanine is used, it (or they) tends (tend) to agglomerate and does (do) not effectively function.

The oxidation reaction may be carried out under normal pressure at about 60 to about 120° C. for about 9 to about 24 hours.

The organic solvent may be benzonitrile, acetonitrile, or a mixture of both.

A flow rate of the oxygen gas for each mole of the secondary or primary alcohol may be from about 2000 to about 4000 mL/min.

In particular, the process comprises introducing the organic solvent, the secondary or primary alcohol, NHPI, and phthalocyanine into a reactor to form a mixture, introducing the oxygen gas into the mixture, and stirring the mixture at a constant temperature, to give the ketone or carboxylic acid.

The secondary alcohol may be cyclohexanol, phenylethanol, or 1-phenyl-1-propanol. The primary alcohol may be butyl alcohol, benzyl alcohol, or 1-dodecanol.

Compared with the prior art, the process of the presently disclosed subject matter has several advantages.

NHPI combined with phthalocyanine is used as a catalytic system by the presently disclosed subject matter for the first time to catalyze oxidation of a secondary or primary alcohol to a ketone or carboxylic acid. It is found that the system has an excellent catalytic effect and the yield of the target product achievable with the catalytic system may be up to about 91.49%.

The catalyst of the presently disclosed subject matter can be readily prepared and recovered, substantially reducing the catalyst cost. So, the catalyst has a good application prospect.

In the process of the presently disclosed subject matter, oxygen gas is employed as the source of the oxidant, which solves the problem of environmental pollution to a certain extent.

DETAILED DESCRIPTION

The presently disclosed subject matter will be explained in more detail below with reference to examples. The following examples serve to provide further appreciation of the presently disclosed subject matter but are not meant in any way to restrict the scope of the presently disclosed subject matter. It should be noted that for those of ordinary skill in the art various modifications and improvements can be made without departing from the concept of the presently disclosed subject matter, and all of the modifications and improvements belong to the protection scope of the presently disclosed subject matter.

In particular, an embodiment of the process for preparing a ketone or carboxylic acid by catalytic oxidation of a secondary or primary alcohol according to the presently disclosed subject matter comprises introducing an organic solvent, the secondary or primary alcohol, NHPI, and phthalocyanine into a reactor to form a mixture, introducing oxygen gas into the mixture, and stirring the mixture at a constant temperature within a range of about 60 to about 120° C. under normal pressure for about 9 to about 36 hours, to give the ketone or carboxylic acid. According to the process, the catalyst comprises NHPI and phthalocyanine. A molar ratio of NHPI to the secondary or primary alcohol may be from about 0.1:1 to about 0.3:1, for example from about 0.2:1 to about 0.3:1. A molar ratio of phthalocyanine to the secondary or primary alcohol may be from about 0.04:1 to about 0.1:1, for example from about 0.08:1 to about 0.1:1. The organic solvent may be benzonitrile, acetonitrile, or a mixture of both. The volume of the organic solvent used for each mole of the secondary or primary alcohol may be from about 1000 to about 1500 mL. A flow rate of the oxygen gas for each mole of the secondary or primary alcohol may be from about 2000 to about 4000 mL/min.

With the process of the presently disclosed subject matter, the primary alcohol can be oxidized to the corresponding carboxylic acid, and the secondary alcohol can be oxidized to the corresponding ketone. A reaction mechanism of the secondary alcohol oxidation according to the presently disclosed subject matter is the same as that of the primary alcohol oxidation. The process of the presently disclosed subject matter is applicable to compounds carrying a primary alcohol group or a secondary alcohol group. The following examples use cyclohexanol, phenylethanol, and 1-phenyl-1-propanol to demonstrate the catalytic effect of the catalyst of the presently disclosed subject matter on the oxidation of the secondary alcohol, and use butyl alcohol, benzyl alcohol, and 1-dodecanol to demonstrate the catalytic effect of the catalyst on the oxidation of the primary alcohol.

In these examples, cyclohexanol was oxidized to cyclohexanone, benzyl alcohol to benzoic acid, phenylethanol to acetophenone, butyl alcohol to butyraldehyde and ethylacetic acid, 1-phenyl-1-propanol to propiophenone, and 1-dodecanol to lauric acid. The products were analyzed by gas chromatography (GC). For the purpose of the quantitative analysis, a yield of cyclohexanone was obtained from an internal standard method (internal standard substance: chlorobenzene), in which an internal standard curve of cyclohexanone and chlorobenzene was created and the yield of cyclohexanone was then calculated based on the curve and results of the GC analysis; a yield of benzoic acid was obtained based on its amount obtained by removal of the solvent by evaporation under a reduced pressure using a rotary evaporator; a yield of acetophenone was obtained from an internal standard method (internal standard substance: benzonitrile), in which an internal standard curve of acetophenone and benzonitrile was created and the yield of acetophenone was then calculated based on the curve and results of the GC analysis; butyraldehyde and ethylacetic acid were analyzed by GC, and their yields were obtained from an area normalization method; a yield of propiophenone was obtained from an internal standard method (internal standard substance: benzonitrile), in which an internal standard curve of propiophenone and benzonitrile was created and the yield of propiophenone was then calculated based on the curve and results of the GC analysis; and lauric acid was analyzed by GC and its yield was obtained from an area normalization method.

The examples of the presently disclosed subject matter will be described below.

Example 1

Tetraamido-substituted cobalt phthalocyanine was synthesized according to a method described in Rezaeifard, M, et al. *Catal. Commun.* 2011, 12: 761. According to this method, 13.8 g of 4-carboxylic-phthalic anhydride, 4.2 g of cobalt chloride ($CoCl_2$), 25 g of urea (with a molar ratio of 4-carboxylic-phthalic anhydride:$CoCl_2$:urea being 4:1:20), 1.9 g of ammonium chloride, and 4.2 g of ammonium molybdate were placed into a mortar and ground sufficiently. The ground mixture was then introduced into a 500 mL heavy wall, three-necked flask to proceed with a reaction at a constant temperature within a range of 130 to 140° C. for 0.5 hour. The reaction mixture was then heated to 180° C., at which it was maintained for another 0.5 hour. A suitable amount of urea was added into the mixture. The mixture was then heated to 220 to 230° C., at which it was maintained for 4 hours. An obtained solid was repeatedly washed with boiling water until a colorless filtrate was obtained, then washed with acetone 3 times, and finally with methanol 3 times. After drying, a blue black solid, that is tetraamido-substituted cobalt phthalocyanine, was obtained.

Comparative Example 1

10 mL of benzonitrile, 1.0021 g of cyclohexanol, 0.3235 g of NHPI, and 0.2973 g of phthalocyanine were introduced into a three-necked flask in sequence. Oxygen gas was then introduced into the mixture in the flask under normal pressure at a flow rate of 20 mL/min. The mixture was stirred at 100° C. for 24 hours. Analysis by GC showed a 41.25% yield of cyclohexanone.

In this example, a ratio of the molar amount of cyclohexanol to the volume of benzonitrile was 1 mol:1000 mL. A molar ratio of NHPI:phthalocyanine:cyclohexanol was 0.2:0.04:1. The flow rate of the oxygen gas was 2000 mL/min for each mole of cyclohexanol.

Comparative Example 2

10 mL of benzonitrile, 1.0036 g of cyclohexanol, 0.1612 g of NHPI, and 0.5934 g of phthalocyanine were introduced into a three-necked flask in sequence. Oxygen gas was then introduced into the mixture in the flask under normal pressure at a flow rate of 20 mL/min. The mixture was stirred at 100° C. for 24 hours. Analysis by GC showed a 11.26% yield of cyclohexanone.

In this example, a ratio of the molar amount of cyclohexanol to the volume of benzonitrile was 1 mol:1000 mL. A molar ratio of NHPI:phthalocyanine:cyclohexanol was 0.1:0.08:1. The flow rate of the oxygen gas was 2000 mL/min for each mole of cyclohexanol.

Example 2

10 mL of benzonitrile, 1.0016 g of cyclohexanol, 0.3224 g of NHPI, and 0.5945 g of phthalocyanine were introduced into a three-necked flask in sequence. Oxygen gas was then introduced into the mixture in the flask under normal pressure at a flow rate of 20 mL/min. The mixture was stirred at 100° C. for 24 hours. Analysis by GC showed a 73.17% yield of cyclohexanone.

In this example, a ratio of the molar amount of cyclohexanol to the volume of benzonitrile was 1 mol:1000 mL. A molar ratio of NHPI:phthalocyanine:cyclohexanol was 0.2:0.08:1. The flow rate of the oxygen gas was 2000 mL/min for each mole of cyclohexanol.

A comparison between Example 2 and Comparative Example 1 shows that the yield of the product decreases significantly with the decrease in the addition amount of phthalocyanine. This demonstrates that an excessively small amount of phthalocyanine is detrimental to the reaction.

A comparison between Example 2 and Comparative Example 2 shows that the yield of the product decreases significantly with the decrease in the addition amount of NHPI. This demonstrates that an excessively small amount of NHPI is detrimental to the reaction.

Example 3

10 mL of acetonitrile, 1.0813 g of benzyl alcohol, 0.3224 g of NHPI, and 0.5945 g of phthalocyanine were introduced into a three-necked flask in sequence. Oxygen gas was then introduced into the mixture in the flask under normal pressure at a flow rate of 20 mL/min. The mixture was stirred at 80° C. for 9 hours. Analysis by GC and by thin layer chromatography (TLC) showed that a final product was benzoic Acid. Acetonitrile was subsequently evaporated off by a rotary evaporator under a reduced pressure. The benzoic Acid yield was calculated to be 86.78%.

In this example, a ratio of the molar amount of benzyl alcohol to the volume of acetonitrile was 1 mol:1000 mL. A molar ratio of NHPI:phthalocyanine:benzyl alcohol was 0.2:0.08:1. The flow rate of the oxygen gas was 2000 mL/min for each mole of benzyl alcohol.

Example 4

15 mL of acetonitrile, 1.1975 g of phenylethanol, 0.3256 g of NHPI, and 0.5846 g of phthalocyanine were introduced into a three-necked flask in sequence. Oxygen gas was then introduced into the mixture in the flask under normal pressure at a flow rate of 20 mL/min. The mixture was stirred at 80° C. for 36 hours. Analysis by GC showed a 91.49% yield of acetophenone.

In this example, a ratio of the molar amount of phenylethanol to the volume of acetonitrile was 1 mol:1500 mL. A molar ratio of NHPI:phthalocyanine:phenylethanol was 0.2:

0.08:1. The flow rate of the oxygen gas was 2000 mL/min for each mole of phenylethanol.

Example 5

15 mL of acetonitrile, 0.74 g of butyl alcohol, 0.3243 g of NHPI, and 0.5882 g of phthalocyanine were introduced into a three-necked flask in sequence. Oxygen gas was then introduced into the mixture in the flask under normal pressure at a flow rate of 20 mL/min. The mixture was stirred at 80° C. for 24 hours. Products were analyzed by GC by comparison with corresponding standards.

The products were separated, and then $^1$H NMR analysis was performed to confirm the structure of the products obtained. It was confirmed by $^1$H NMR that the products obtained were butyraldehyde and butyric acid. The yields of butyraldehyde and butyric acid obtained from an area normalization method were 27.77% and 66.47%, respectively, with a total yield of 94.24%.

In this example, a ratio of the molar amount of butyl alcohol to the volume of acetonitrile was 1 mol:1500 mL. A molar ratio of NHPI:phthalocyanine:butyl alcohol was 0.2:0.08:1. The flow rate of the oxygen gas was 2000 mL/min for each mole of butyl Alcohol.

Example 6

15 mL of acetonitrile, 1.3502 g of 1-phenyl-1-propanol, 0.3253 g of NHPI, and 0.5982 g of phthalocyanine were introduced into a three-necked flask in sequence. Oxygen gas was then introduced into the mixture in the flask under normal pressure at a flow rate of 20 mL/min. The mixture was stirred at 80° C. for 24 hours. Products were analyzed by GC by comparison with corresponding standards. A product was separated and confirmed to be propiophenone. The yield of propiophenone was 77.24%.

In this example, a ratio of the molar amount of 1-phenyl-1-propanol to the volume of acetonitrile was 1 mol:1500 mL. A molar ratio of NHPI:phthalocyanine: 1-phenyl-1-propanol was 0.2:0.08:1. The flow rate of the oxygen gas was 2000 mL/min for each mole of 1-phenyl-1-propanol.

Example 7

15 mL of acetonitrile, 1.8603 g of 1-dodecano, 0.3213 g of NHPI, and 0.5926 g of phthalocyanine were introduced into a three-necked flask in sequence. Oxygen gas was then introduced into the mixture in the flask under normal pressure at a flow rate of 20 mL/min. The mixture was stirred at 80° C. for 24 hours. Products were analyzed by GC by comparison with corresponding standards. A product was separated, and then $^1$H NMR analysis was performed to confirm the structure of the product obtained. It was confirmed by $^1$H NMR that the product obtained was lauric acid. The yield of lauric acid was 82.44%.

In this example, a ratio of the molar amount of 1-dodecano to the volume of acetonitrile was 1 mol:1500 mL. A molar ratio of NHPI:phthalocyanine: 1-dodecano was 0.2:0.08:1. The flow rate of the oxygen gas was 2000 mL/min for each mole of 1-dodecano.

Example 8

10 mL of benzonitrile, 1.0016 g of cyclohexanol, 0.1612 g of NHPI, and 0.2972 g of phthalocyanine were introduced into a three-necked flask in sequence. Oxygen gas was then introduced into the mixture in the flask under normal pressure at a flow rate of 20 mL/min. The mixture was stirred at 60° C. for 24 hours. Analysis by GC showed a 23.72% yield of cyclohexanone.

In this example, a ratio of the molar amount of cyclohexanol to the volume of benzonitrile was 1 mol:1000 mL. A molar ratio of NHPI:phthalocyanine:cyclohexanol was 0.2:0.04:1. The flow rate of the oxygen gas was 4000 mL/min for each mole of cyclohexanol.

Example 9

10 mL of benzonitrile, 1.0016 g of cyclohexanol, 0.4836 g of NHPI, and 0.7431 g of phthalocyanine were introduced into a three-necked flask in sequence. Oxygen gas was then introduced into the mixture in the flask under normal pressure at a flow rate of 20 mL/min. The mixture was stirred at 120° C. for 24 hours. Analysis by GC showed a 65.17% yield of cyclohexanone.

In this example, a ratio of the molar amount of cyclohexanol to the volume of benzonitrile was 1 mol:1000 mL. A molar ratio of NHPI:phthalocyanine:cyclohexanol was 0.3:0.1:1. The flow rate of the oxygen gas was 2000 mL/min for each mole of cyclohexanol.

Description of embodiments of the presently disclosed subject matter is given above. However, the invention is not limited to these particular disclosed embodiments. Those of ordinary skill in the art can understand that various variations and modifications can be made within the scope of the presently disclosed subject matter, which does not affect the substantive content of the presently disclosed subject matter.

What is claimed is:

1. A process for preparing a ketone or carboxylic acid by catalytic oxidation of a secondary or primary alcohol, comprising adding the secondary or primary alcohol and N-hydroxyphthalimide (NHPI) combined with phthalocyanine, serving as a catalytic system, into an organic solvent into which oxygen gas is then introduced, to proceed with an oxidation reaction to give the ketone or carboxylic acid.

2. The process according to claim 1, wherein the catalytic system, NHPI combined with phthalocyanine, comprises NHPI and phthalocyanine, wherein a molar ratio of NHPI to the secondary or primary alcohol is from 0.1:1 to 0.3:1, and a molar ratio of phthalocyanine to the secondary or primary alcohol is from 0.04:1 to 0.1:1.

3. The process according to claim 2, wherein the molar ratio of NHPI to the secondary or primary alcohol is from 0.2:1 to 0.3:1, and the molar ratio of phthalocyanine to the secondary to primary alcohol is from 0.08:1 to 0.1:1.

4. The process according to claim 1, wherein the oxidation reaction is carried out under normal pressure at 60 to 120° C. for 9 to 36 hours.

5. The process according to claim 1, wherein the organic solvent is benzonitrile, acetonitrile, or a mixture of both.

6. The process according to claim 1, wherein the volume of the organic solvent used for each mole of the secondary or primary alcohol is from 1000 to 1500 mL.

7. The process according to claim 1, wherein a flow rate of the oxygen gas for each mole of the secondary or primary alcohol is from 2000 to 4000 mL/min.

8. The process according to claim 1, comprising:
introducing the organic solvent, the secondary or primary alcohol, NHPI, and phthalocyanine into a reactor to form a mixture,
introducing the oxygen gas into the mixture, and
stirring the mixture at a constant temperature to give the ketone or carboxylic acid.

9. The process according to claim 1, wherein the secondary alcohol is cyclohexanol, phenylethanol, or 1-phenyl-1-propanol, and the primary alcohol is butyl alcohol, benzyl alcohol, or 1-dodecanol.

\* \* \* \* \*